US008344186B2

(12) United States Patent
Jevtic et al.

(10) Patent No.: US 8,344,186 B2
(45) Date of Patent: Jan. 1, 2013

(54) PROCESSES FOR PRODUCING ETHANOL FROM ACETALDEHYDE

(75) Inventors: Radmila Jevtic, Houston, TX (US); Victor J. Johnston, Houston, TX (US); Lincoln Sarager, Houston, TX (US); R. Jay Warner, Houston, TX (US); Heiko Weiner, Pasadena, TX (US); Trinity Horton, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 0 days.

(21) Appl. No.: 12/915,625

(22) Filed: Oct. 29, 2010

(65) Prior Publication Data
US 2011/0190551 A1 Aug. 4, 2011

Related U.S. Application Data

(63) Continuation-in-part of application No. 12/852,269, filed on Aug. 6, 2010.

(60) Provisional application No. 61/300,815, filed on Feb. 2, 2010, provisional application No. 61/332,699, filed on May 7, 2010.

(51) Int. Cl.
C07C 29/141 (2006.01)

(52) U.S. Cl. .......................... 568/881; 568/882; 568/883

(58) Field of Classification Search .................. 568/881, 568/882, 883
See application file for complete search history.

(56) References Cited

U.S. PATENT DOCUMENTS

| | | |
|---|---|---|
| 2,021,698 A | 11/1935 | Perkins |
| 2,105,540 A | 1/1938 | Lazier |
| 2,425,389 A | 8/1947 | Oxley et al. |
| 2,549,416 A | 4/1951 | Brooks |
| 2,607,807 A | 8/1952 | Ford |
| 2,649,407 A | 8/1953 | Harrison et al. |
| 2,702,783 A | 2/1955 | Harrison et al. |
| 2,744,939 A | 5/1956 | Kennel |
| 2,859,241 A | 11/1958 | Schnizer |
| 2,882,244 A | 4/1959 | Milton |
| 3,130,007 A | 4/1964 | Breck |
| 3,408,267 A | 10/1968 | Miller et al. |
| 3,445,345 A | 5/1969 | Katzen et al. |
| 3,450,748 A * | 6/1969 | Schaeffer ...................... 560/243 |
| 3,478,112 A | 11/1969 | Karl et al. |
| 3,702,886 A | 11/1972 | Argauer et al. |
| 3,729,429 A | 4/1973 | Robson |
| 3,953,524 A | 4/1976 | Steiner |
| 3,990,952 A | 11/1976 | Katzen et al. |
| 4,052,467 A | 10/1977 | Mills et al. |
| 4,065,512 A | 12/1977 | Cares |
| 4,228,307 A | 10/1980 | Zimmerschied |
| 4,270,015 A | 5/1981 | Knifton et al. |
| 4,275,228 A | 6/1981 | Gruffaz et al. |
| 4,306,942 A | 12/1981 | Brush et al. |
| 4,317,918 A | 3/1982 | Takano et al. |
| 4,319,058 A | 3/1982 | Kulprathipanja et al. |
| 4,328,373 A | 5/1982 | Strojny |
| 4,337,351 A | 6/1982 | Larkins |
| 4,374,265 A | 2/1983 | Larkins, Jr. |
| 4,379,028 A | 4/1983 | Berg et al. |
| 4,395,576 A | 7/1983 | Kwantes et al. |
| 4,398,039 A | 8/1983 | Pesa et al. |
| 4,399,305 A | 8/1983 | Schreck et al. |
| 4,421,939 A | 12/1983 | Kiff et al. |
| 4,422,903 A | 12/1983 | Messick et al. |
| 4,426,541 A | 1/1984 | King |
| 4,443,639 A | 4/1984 | Pesa et al. |
| 4,451,677 A | 5/1984 | Bradley et al. |
| 4,454,358 A | 6/1984 | Kummer et al. |
| 4,465,854 A | 8/1984 | Pond et al. |
| 4,471,136 A | 9/1984 | Larkins et al. |
| 4,480,115 A | 10/1984 | McGinnis |
| 4,492,808 A | 1/1985 | Hagen et al. |
| 4,497,967 A | 2/1985 | Wan |
| 4,517,391 A | 5/1985 | Schuster et al. |
| 4,520,213 A | 5/1985 | Victor |
| 4,521,630 A | 6/1985 | Wattimena et al. |
| 4,541,897 A | 9/1985 | Sommer et al. |
| 4,550,185 A | 10/1985 | Mabry et al. |
| 4,581,473 A | 4/1986 | Polichnowski et al. |
| 4,613,700 A | 9/1986 | Maki et al. |
| 4,620,050 A | 10/1986 | Cognion et al. |
| 4,626,321 A | 12/1986 | Grethlein et al. |
| 4,626,604 A | 12/1986 | Hiles et al. |
| 4,678,543 A | 7/1987 | Houben et al. |
| 4,692,218 A | 9/1987 | Houben et al. |
| 4,696,596 A | 9/1987 | Russell et al. |
| 4,710,086 A | 12/1987 | Naaktgeboren et al. |

(Continued)

FOREIGN PATENT DOCUMENTS

CN 1230458 10/1999

(Continued)

OTHER PUBLICATIONS

Cumming et al., English abstract of foreign Patent document DE 1907120 A.* U.S. Appl. No. 12/852,227, Jevtic, et al.
U.S. Appl. No. 12/852,269, Jevtic, et al.
U.S. Appl. No. 12/833,737, Johnston, et al.
Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.
ZeaChem, Inc., Technology Overview, Lakewood, Colorado www.zeachem.com, 2008.
Santori et al.(2000). Hydrogenation of carbonylic compounds on Pt/SiO2 catalysts modified with SnBu4, Studies in Surface Science and Catalysis, 130, 2063-2068.
(2000). Hydrogenation of carbonylic compounds on Pt/SiO2 catalysts modified with SnBu4, Studies in Surface Science and Catalysis, 130, 2063-2068.
Rachmady, Acetic Acid Reduction by H2 on Bimetallic Pt—Fe Catalysts, Journal of Catalysis 209, 87-98 (Apr. 1, 2002), Elsevier Science (USA).

(Continued)

*Primary Examiner* — Elvis O Price

(57) ABSTRACT

In one embodiment, the invention is to a process for forming an ethanol mixture by hydrogenating an acetaldehyde feed stream in the presence of a catalyst. The acetaldehyde feed stream comprises acetaldehyde and at least one of acetic acid and ethanol. Preferably the acetaldehyde feed stream is a by-product stream from a vinyl acetate synthesis process.

18 Claims, 2 Drawing Sheets

U.S. PATENT DOCUMENTS

| | | | |
|---|---|---|---|
| 4,762,817 A | 8/1988 | Logsdon et al. | |
| 4,777,303 A | 10/1988 | Kitson et al. | |
| 4,804,791 A | 2/1989 | Kitson et al. | |
| 4,826,795 A | 5/1989 | Kitson et al. | |
| 4,842,693 A | 6/1989 | Wheldon | |
| 4,843,170 A | 6/1989 | Isshiki et al. | |
| 4,876,402 A | 10/1989 | Logsdon et al. | |
| 4,886,905 A | 12/1989 | Larkins et al. | |
| 4,902,823 A | 2/1990 | Wunder et al. | |
| 4,961,826 A | 10/1990 | Grethlein et al. | |
| 4,978,778 A | 12/1990 | Isshiki et al. | |
| 4,985,572 A | 1/1991 | Kitson et al. | |
| 4,990,655 A | 2/1991 | Kitson et al. | |
| 4,994,608 A | 2/1991 | Torrence et al. | |
| 5,001,259 A | 3/1991 | Smith et al. | |
| 5,004,845 A | 4/1991 | Bradley et al. | |
| 5,026,908 A | 6/1991 | Smith et al. | |
| 5,035,776 A | 7/1991 | Knapp | |
| 5,061,671 A | 10/1991 | Kitson et al. | |
| 5,070,016 A | 12/1991 | Hallberg et al. | |
| 5,093,534 A | 3/1992 | Ludwig et al. | |
| 5,124,004 A | 6/1992 | Grethlein et al. | |
| 5,137,861 A | 8/1992 | Shih et al. | |
| 5,144,068 A | 9/1992 | Smith et al. | |
| 5,149,680 A | 9/1992 | Kitson et al. | |
| 5,155,084 A | 10/1992 | Horn et al. | |
| 5,185,308 A | 2/1993 | Bartley et al. | |
| 5,185,481 A | 2/1993 | Muto et al. | |
| 5,198,592 A | 3/1993 | Van Beijnum et al. | |
| 5,233,099 A | 8/1993 | Tabata et al. | |
| 5,237,108 A | 8/1993 | Marraccini et al. | |
| 5,241,106 A | 8/1993 | Inoue et al. | |
| 5,243,095 A | 9/1993 | Roberts et al. | |
| 5,250,271 A | 10/1993 | Horizoe et al. | |
| 5,306,845 A | 4/1994 | Yokohama et al. | |
| 5,334,769 A | 8/1994 | Ferrero et al. | |
| 5,348,625 A | 9/1994 | Berg | |
| 5,350,504 A | 9/1994 | Dessau | |
| 5,415,741 A | 5/1995 | Berg | |
| 5,426,246 A | 6/1995 | Nagahara et al. | |
| 5,437,770 A | 8/1995 | Berg | |
| 5,445,716 A | 8/1995 | Berg | |
| 5,449,440 A | 9/1995 | Rescalli et al. | |
| 5,475,144 A | 12/1995 | Watson et al. | |
| 5,476,827 A | 12/1995 | Ferrero et al. | |
| RE35,377 E | 11/1996 | Steinberg et al. | |
| 5,585,523 A | 12/1996 | Weiguny et al. | |
| 5,599,976 A | 2/1997 | Scates et al. | |
| 5,674,800 A | 10/1997 | Abel et al. | |
| 5,691,267 A | 11/1997 | Nicolau et al. | |
| 5,719,315 A | 2/1998 | Tustin et al. | |
| 5,731,456 A | 3/1998 | Tustin et al. | |
| 5,762,765 A | 6/1998 | Berg | |
| 5,767,307 A | 6/1998 | Ramprasad et al. | |
| 5,770,770 A | 6/1998 | Kim et al. | |
| 5,821,111 A | 10/1998 | Grady et al. | |
| 5,845,570 A | 12/1998 | Isozaki et al. | |
| 5,849,657 A | 12/1998 | Rotgerink et al. | |
| 5,861,530 A | 1/1999 | Atkins et al. | |
| 5,955,397 A | 9/1999 | Didillon et al. | |
| 5,973,193 A | 10/1999 | Crane et al. | |
| 6,040,474 A | 3/2000 | Jobson et al. | |
| 6,049,008 A | 4/2000 | Roberts et al. | |
| 6,093,845 A | 7/2000 | Van Acker et al. | |
| 6,114,571 A | 9/2000 | Abel et al. | |
| 6,121,498 A | 9/2000 | Tustin et al. | |
| 6,143,930 A | 11/2000 | Singh et al. | |
| 6,232,352 B1 | 5/2001 | Vidalin et al. | |
| 6,232,504 B1 | 5/2001 | Barteau et al. | |
| 6,294,703 B1 | 9/2001 | Hara et al. | |
| 6,462,231 B1 | 10/2002 | Yanagawa et al. | |
| 6,472,555 B2 | 10/2002 | Choudary et al. | |
| 6,476,261 B2 | 11/2002 | Ellis et al. | |
| 6,486,366 B1 | 11/2002 | Ostgard et al. | |
| 6,495,730 B1 | 12/2002 | Konishi et al. | |
| 6,509,180 B1 | 1/2003 | Verser et al. | |
| 6,509,290 B1 | 1/2003 | Vaughn et al. | |
| 6,559,333 B1 | 5/2003 | Brunelle et al. | |
| 6,603,038 B1 | 8/2003 | Hagemeyer et al. | |
| 6,627,770 B1 | 9/2003 | Cheung et al. | |
| 6,632,330 B1 | 10/2003 | Colley et al. | |
| 6,657,078 B2 | 12/2003 | Scates et al. | |
| 6,685,754 B2 | 2/2004 | Kindig et al. | |
| 6,693,213 B1 | 2/2004 | Kolena et al. | |
| 6,696,596 B1 | 2/2004 | Herzog et al. | |
| 6,723,886 B2 | 4/2004 | Allison et al. | |
| 6,727,380 B2 | 4/2004 | Ellis et al. | |
| 6,765,110 B2 | 7/2004 | Warner et al. | |
| 6,768,021 B2 | 7/2004 | Horan et al. | |
| 6,809,217 B1 | 10/2004 | Colley et al. | |
| 6,812,372 B2 | 11/2004 | Janssen et al. | |
| 6,852,877 B1 | 2/2005 | Zeyss et al. | |
| 6,903,045 B2 | 6/2005 | Zoeller et al. | |
| 6,906,228 B2 | 6/2005 | Fischer et al. | |
| 6,927,048 B2 | 8/2005 | Verser et al. | |
| 7,005,541 B2 | 2/2006 | Cheung et al. | |
| 7,074,603 B2 | 7/2006 | Verser et al. | |
| 7,084,312 B1 | 8/2006 | Huber et al. | |
| 7,115,772 B2 | 10/2006 | Picard et al. | |
| 7,208,624 B2 | 4/2007 | Scates et al. | |
| 7,297,236 B1 | 11/2007 | Vander et al. | |
| 7,351,559 B2 | 4/2008 | Verser et al. | |
| 7,375,049 B2 | 5/2008 | Hayes et al. | |
| 7,425,657 B1 | 9/2008 | Elliott et al. | |
| 7,507,562 B2 | 3/2009 | Verser et al. | |
| 7,518,014 B2 | 4/2009 | Kimmich et al. | |
| 7,538,060 B2 | 5/2009 | Barnicki et al. | |
| 7,553,397 B1 | 6/2009 | Colley et al. | |
| 7,572,353 B1 | 8/2009 | Vander et al. | |
| 7,608,744 B1 | 10/2009 | Johnston et al. | |
| 7,700,814 B2 | 4/2010 | Garton et al. | |
| 7,744,727 B2 | 6/2010 | Blum et al. | |
| 7,790,938 B2 | 9/2010 | Kawasaki et al. | |
| 7,842,844 B2 | 11/2010 | Atkins | |
| 2003/0013908 A1 | 1/2003 | Horan et al. | |
| 2003/0077771 A1 | 4/2003 | Verser et al. | |
| 2003/0104587 A1 | 6/2003 | Verser et al. | |
| 2003/0114719 A1 | 6/2003 | Fischer et al. | |
| 2003/0191020 A1 | 10/2003 | Bharadwaj et al. | |
| 2004/0195084 A1 | 10/2004 | Hetherington et al. | |
| 2006/0019360 A1 | 1/2006 | Verser et al. | |
| 2006/0127999 A1 | 6/2006 | Verser et al. | |
| 2007/0031954 A1 | 2/2007 | Mairal et al. | |
| 2007/0106246 A1 | 5/2007 | Modesitt | |
| 2007/0270511 A1 | 11/2007 | Melnichuk et al. | |
| 2008/0135396 A1 | 6/2008 | Blum | |
| 2008/0207953 A1 | 8/2008 | Houssin et al. | |
| 2009/0005588 A1 | 1/2009 | Hassan et al. | |
| 2009/0014313 A1 | 1/2009 | Lee et al. | |
| 2009/0023192 A1 | 1/2009 | Verser et al. | |
| 2009/0081749 A1 | 3/2009 | Verser et al. | |
| 2009/0166172 A1 | 7/2009 | Casey et al. | |
| 2009/0221725 A1 | 9/2009 | Chornet et al. | |
| 2009/0318573 A1 | 12/2009 | Stites et al. | |
| 2009/0326080 A1 | 12/2009 | Chornet et al. | |
| 2010/0016454 A1 | 1/2010 | Gracey et al. | |
| 2010/0029980 A1 | 2/2010 | Johnston et al. | |
| 2010/0029993 A1 | 2/2010 | Johnston et al. | |
| 2010/0029995 A1 | 2/2010 | Johnston et al. | |
| 2010/0030001 A1 | 2/2010 | Chen et al. | |
| 2010/0030002 A1 | 2/2010 | Johnston et al. | |
| 2010/0069514 A1 | 3/2010 | Gracey et al. | |
| 2010/0113843 A1 | 5/2010 | Lee et al. | |
| 2010/0121114 A1 | 5/2010 | Johnston et al. | |
| 2010/0125148 A1 | 5/2010 | Johnston et al. | |
| 2010/0137630 A1 | 6/2010 | Garton et al. | |
| 2010/0168466 A1 | 7/2010 | Johnston et al. | |
| 2010/0168493 A1 | 7/2010 | Le Peltier et al. | |
| 2010/0185021 A1 | 7/2010 | Ross et al. | |
| 2010/0196789 A1 | 8/2010 | Fisher et al. | |
| 2010/0197485 A1 | 8/2010 | Johnston et al. | |
| 2010/0197959 A1 | 8/2010 | Johnston et al. | |
| 2010/0197985 A1 | 8/2010 | Johnston et al. | |
| 2010/0249479 A1 | 9/2010 | Berg-Slot et al. | |
| 2011/0004033 A1 | 1/2011 | Johnston et al. | |
| 2011/0046421 A1 | 2/2011 | Daniel et al. | |
| 2011/0071312 A1 | 3/2011 | Johnston et al. | |

| | | |
|---|---|---|
| 2011/0082322 A1 | 4/2011 | Jevtic et al. |
| 2011/0190547 A1 | 8/2011 | Jevtic et al. |
| 2011/0190548 A1 | 8/2011 | Jevtic et al. |

FOREIGN PATENT DOCUMENTS

| | | |
|---|---|---|
| DE | 1907120 A * | 10/1970 |
| EP | 0104197 | 4/1984 |
| EP | 0137749 | 4/1985 |
| EP | 0167300 | 1/1986 |
| EP | 0175558 | 3/1986 |
| EP | 0192587 | 8/1986 |
| EP | 0198682 | 10/1986 |
| EP | 0285420 | 10/1988 |
| EP | 0285786 | 10/1988 |
| EP | 0330853 | 9/1989 |
| EP | 0400904 | 5/1990 |
| EP | 0372847 | 6/1990 |
| EP | 0408528 | 7/1990 |
| EP | 0456647 | 11/1991 |
| EP | 0539274 | 4/1993 |
| EP | 0953560 | 11/1999 |
| EP | 0990638 | 4/2000 |
| EP | 1277826 | 1/2003 |
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| GB | 1168785 | 10/1969 |
| GB | 1559540 | 1/1980 |
| GB | 2136704 | 9/1984 |
| JP | 4-193304 | 7/1992 |
| JP | 6-116182 | 4/1994 |
| JP | 10-306047 | 11/1998 |
| JP | 2001-046874 | 2/2001 |
| JP | 2001-157841 | 6/2001 |
| WO | WO 83/03409 | 10/1983 |
| WO | WO 99/08791 | 2/1999 |
| WO | WO 03/040037 | 5/2003 |
| WO | WO 2007003897 A1 * | 1/2007 |
| WO | WO 2008/135912 | 11/2008 |
| WO | WO 2009/009322 | 1/2009 |
| WO | WO 2009/009323 | 1/2009 |
| WO | WO 2009/048335 | 4/2009 |
| WO | WO 2009/063176 | 5/2009 |
| WO | WO 2009/105860 | 9/2009 |
| WO | WO 2010/014148 | 2/2010 |
| WO | WO 2010/014151 | 2/2010 |
| WO | WO 2010/014152 | 2/2010 |
| WO | WO 2010/055285 | 5/2010 |
| WO | WO 2010/056299 | 5/2010 |
| WO | WO 2011/053365 | 5/2011 |

OTHER PUBLICATIONS

Pestman et al., The formation of ketones and aldehydes from carboxylic acids, structure-activity relationship for two competitive reactions, Journal of Molecular Catalysis A: Chemical 103 Jun. 14, 1995, 175-180.

Pestman et al., Reactions of Carboxylic Acids on Oxides, Journal of Catalysis 168:255-264 (1997).

Pestman et al., Identification of the Active Sites in the Selective Hydrogenation of Acetic Acid to Acetaldehyde on Iron Oxide Catalysts, Journal of Catalysis 174:142-152 (1998).

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Ordóñez et al., The role of metal and support sites on the hydrogenation of acetic acid on Ru-based catalysts, 21st NAM San Francisco, CA, Jun. 10, 2009.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.

Acala, et al., (2005). Experimental and DFT studies of the conversion of ethanol and acetic acid on PtSn-based catalysts, Journal of Physical Chemistry, 109(6), 2074-2085.

Proc. Roy Soc. A314, pp. 473-498 (1970).

Djerboua, et al., "On the performance of a highly loadedCO/SiO2 catalyst in the gas phase hydrogenation of crotonaldehyde thermal treatments—catalyst structure-selectivity relationship," Applied Catalysis A: General (2005), 282, p. 123-133.

Liberkova, and Tourounde, "Performance of Pt/SnO2 catalyst in the gas phase hydrogenation of crotonaldehyde," J. Mol. Catal. A: Chemical (2002), 180, p. 221-230.

Rodrigues and Bueno, "Co/SiO2 catalysts for selective hydrogenation of crotonaldehyde: III. Promoting effect of zinc," Applied Catalysis A: General (2004), 257, p. 210-211.

Ammari, et al. "An emergent catalytic material: Pt/ZnO catalyst for selective hydrogenation of crotonaldehyde," J. Catal. (2004), 221, p. 32-42.

Ammari, et al. "Selective hydrogenation of crotonaldehyde on Pt/ZnCl2/SiO2 catalysts," J. Catal. (2005), 235, p. 1-9.

Consonni, et al. "High Performances of Pt/ZnO Catalysts in Selective Hydrogenation of Crotonaldehyde," J. Catal. (1999), 188, p. 165-175.

Nitta, et al. "Selective hydrogenation of αβ-unsaturated aldehydes on cobalt—silica catalysts obtained from cobalt chrysotile," Applied Catal. (1989), 56, p. 9-22.

International Search Report and Written Opinion for PCT/US2009/004197 mailed Mar. 24, 2010 (14 pages).

International Search Report and Written Opinion for PCT/US2009/004195 mailed Mar. 26, 2010 (12 pages).

Written Opinion for PCT/US2011/023331 mailed Feb. 2, 2012.

Hilmen, "Separation of Azeotropic Mixtures: Tools for Analysis and Studies on Batch Distillation Operation", (Nov. 2000) p. 17-20.

Invitation to Pay Additional Fees and Partial Search Report for PCT/US2011/023331 mailed May 4, 2011.

English Abstract for CN1230458.

English Abstract for EP0456647.

English Abstract for WO 2008/135192.

International Preliminary Report on Patentability mailed May 14, 2012 in corresponding International Application No. PCT/US2011/023331.

International Written Opinion mailed May 8, 2012 in corresponding International Application No. PCT/US2011/023272.

International Preliminary Report on Patentability mailed May 18, 2012 in International Application No. PCT/US2010/054136.

International Search Report and Written Opinion mailed Jan. 18, 2012 in corresponding International Application No. PCT/US2011/035577.

International Search Report mailed Aug. 11, 2011 in corresponding International Application No. PCT/US2011/023272.

International Search Report and Written Opinion mailed Jul. 14, 2011 in corresponding International Application No. PCT/US2010/054136.

Brunauer Emmett and Teller, J. Am. Chem. Soc. 60, 309 (1938).

International Preliminary Report on Patentability for PCT/US2011/023272 mailed Jun. 26, 2012.

* cited by examiner

PROCESSES FOR PRODUCING ETHANOL FROM ACETALDEHYDE

CROSS REFERENCE TO RELATED APPLICATIONS

This application is a continuation-in-part of and claims priority to U.S. application Ser. No. 12/852,269, filed on Aug. 6, 2010, which claims priority to U.S. Provisional Application No. 61/300,815, filed on Feb. 2, 2010, and U.S. Provisional Application No. 61/332,699, filed on May 7, 2010. These applications are incorporated herein by reference.

FIELD OF THE INVENTION

The present invention relates generally to processes for hydrogenating an acetaldehyde feed steam in the presence of a catalyst to form an ethanol mixture.

BACKGROUND OF THE INVENTION

Ethanol for industrial use is conventionally produced from petrochemical feed stocks, such as oil, natural gas, or coal; from feed stock intermediates, such as syngas; or from starchy materials or cellulosic materials, such as corn or sugar cane. Conventional methods for producing ethanol from petrochemical feed stocks, as well as from cellulosic materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol. When feed stock prices rise, the need for alternative sources of ethanol production becomes more evident. Starchy materials, as well as cellulosic materials, are converted to ethanol by fermentation. However, fermentation is typically used for consumer production of ethanol for fuels or consumption. In addition, fermentation of starchy or cellulosic materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are often formed with ethanol or are formed in side reactions. For example, during hydrogenation, esters are produced that together with ethanol and/or water form azeotropes, which are difficult to separate. These impurities may limit the production of ethanol and may require expensive and complex purification trains to separate the impurities from the ethanol. Also, the hydrogenation of acetic acid typically yields ethanol and water along with small amounts of side reaction-generated impurities and/or by-products. At maximum theoretical conversion and selectivity, the crude ethanol product would comprise approximately 72 wt. % ethanol and 28 wt. % water. In order to form purified ethanol, much of the water that is co-produced must be removed from the crude ethanol composition. In addition, when conversion is incomplete, unreacted acid may remain in the crude ethanol product. It is typically desirable to remove this residual acetic acid from the crude ethanol product to yield purified ethanol.

It is also well known to reduce, e.g., hydrogenate, aldehydes to their corresponding alcohol. Thus, ethanol may be formed via the hydrogenation of acetaldehyde. Exemplary aldehyde hydrogenation processes are described in U.S. Pat. Nos. 5,093,534; 5,004,845; 4,876,402; 4,762,817; 4,626,604; 4,451,677; 4,426,541; 4,052,467; 3,953,524; and 2,549,416, the entireties of which are incorporated herein by reference.

As an example, crotonaldehyde may be hydrogenated to form crotyl alcohol. The following references relate to this reaction: (1) Djerboua, et al. "On the performance of a highly loadedCO/$SiO_2$ catalyst in the gas phase hydrogenation of crotonaldehyde thermal treatments—catalyst structure-selectivity relationship," *Applied Catalysis A: General* (2005), 282, pg 123-133; (2) Liberkova, and Tourounde, "Performance of Pt/$SnO_2$ catalyst in the gas phase hydrogenation of crotonaldehyde," *J. Mol. Catal. A: Chemical* (2002), 180, pg. 221-230; (3) Rodrigues and Bueno, "Co/$SiO_2$ catalysts for selective hydrogenation of crotonaldehyde: III. Promoting effect of zinc," *Applied Catalysis A: General* (2004), 257, pg. 210-211; (4) Ammari, et al., "An emergent catalytic material: Pt/ZnO catalyst for selective hydrogenation of crotonaldehyde," *J. Catal.* (2004), 221, pg. 32-42; (5) Ammari, et al., "Selective hydrogenation of crotonaldehyde on Pt/$ZnCl_2$/$SiO_2$ catalysts," J. Catal. (2005), 235, pg. 1-9; (6) Consonni, et al. "High Performances of Pt/ZnO Catalysts in Selective Hydrogenation of Crotonaldehyde," *J. Catal.* (1999), 188, pg. 165-175; and (7) Nitta, et al., "Selective hydrogenation of αβ-unsaturated aldehydes on cobalt-silica catalysts obtained from cobalt chrysotile," *Applied Catal.* (1989), 56, pg. 9-22.

Even in view of these teachings, the need remains for improved processes for producing ethanol via acetaldehyde hydrogenation, which have high ethanol production efficiencies.

SUMMARY OF THE INVENTION

The present invention relates to processes for producing an ethanol mixture. The process comprises the step of hydrogenating an acetaldehyde feed stream in the presence of a catalyst to form the ethanol mixture. The catalyst comprises a first metal, a silicaceous support, and at least one support modifier. The acetaldehyde feed stream comprises acetaldehyde and at least one of acetic acid and ethanol. Preferably, the acetaldehyde feed stream comprises from 25 wt. % to 90 wt. % of acetaldehyde and from 10 wt. % to 75 wt. % of acetic acid and/or ethanol. The ethanol mixture, as prepared by the inventive process, preferably comprises from 50 wt. % to 97 wt. % ethanol; from 0.1 wt. % to 25 wt. % water; less than 35 wt. % acetic acid; and less than 10 wt. % acetaldehyde. Preferably, the conversion of the acetaldehyde in the acetaldehyde feed stream is at least 75% and the conversion of the acetic acid in the acetaldehyde feed stream is at least 10%. Preferably, the catalyst is highly selective in converting acetaldehyde and acetic acid to ethanol. Preferably, the catalyst used in converting acetaldehyde and/or acetic acid to ethanol provides for a selectivity to ethanol of at least 80%, e.g., at least 85%, at least 88%, at least 90%, or at least 95%.

In another embodiment, the process comprises the step of contacting a mixture of ethylene and acetic acid with oxygen to produce vinyl acetate and at least one by-product stream comprising acetaldehyde, e.g., from 90 wt. % to 99.9 wt. % acetaldehyde. The process further comprises the step of reacting, e.g., hydrogenating, at least a portion of the at least one by-product stream in the presence of a catalyst to form the ethanol mixture. Preferably, the at least one by-product stream is co-vaporized with a separate feed stream comprising at least one of acetic acid and ethanol to form a vapor feed stream, which is directed to a hydrogenation reactor for hydrogenation over the catalyst to form ethanol.

BRIEF DESCRIPTION OF DRAWINGS

The invention is described in detail below with reference to the appended drawings, wherein like numerals designate similar parts.

DETAILED DESCRIPTION OF THE INVENTION

Figure 1:
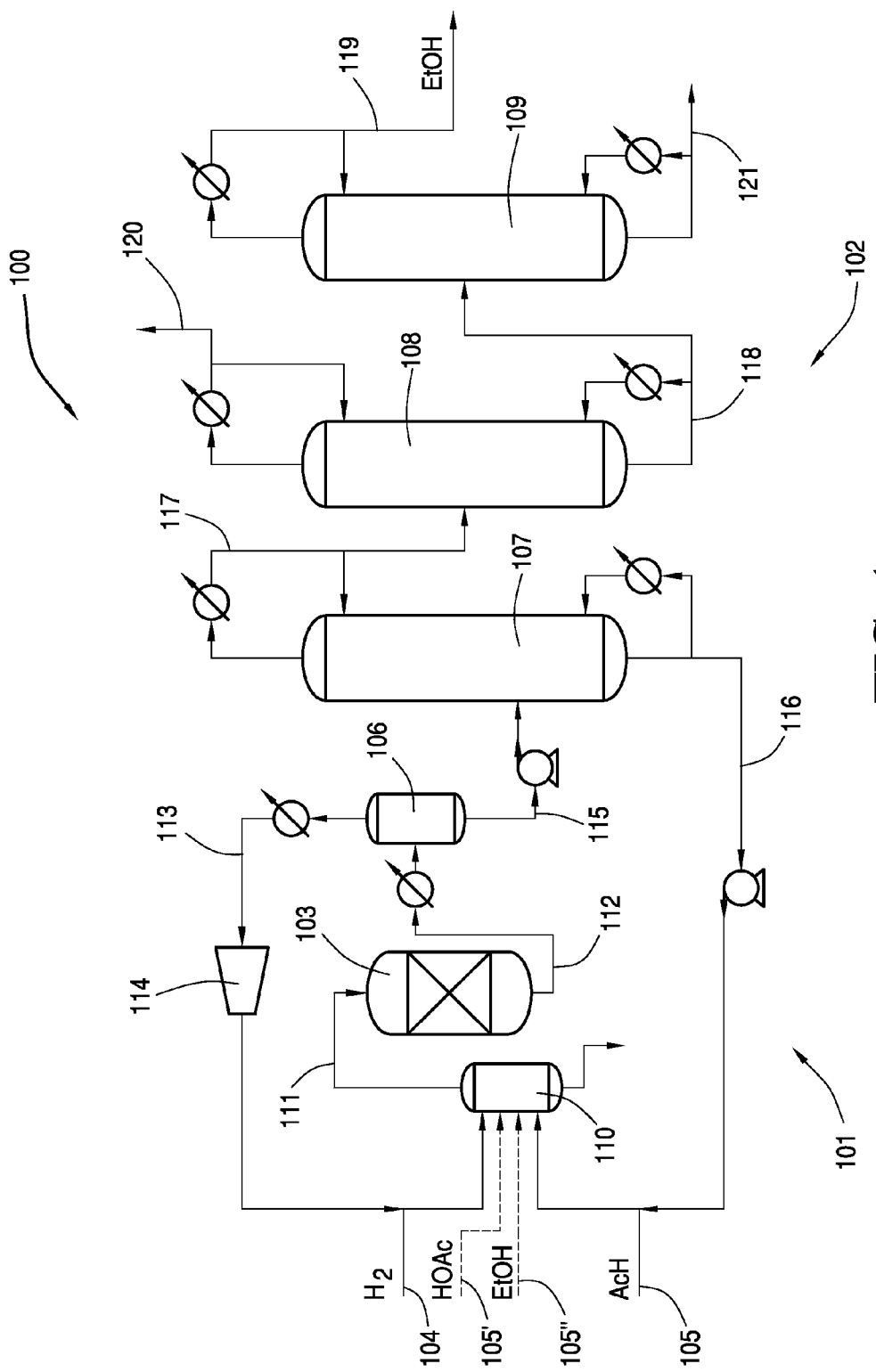
FIG. 1 is a schematic diagram of a hydrogenation system having three separation columns in accordance with one embodiment of the present invention.

Ethanol (and water) may be formed, for example, via the hydrogenation of acetic acid as represented by the following reaction:

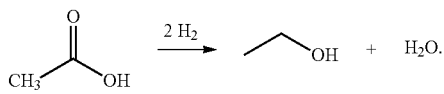

This reaction, however, often yields impurities and/or by-products that are generated via side reactions. As such, significant purification trains may be necessary to form a purified ethanol composition. Also, the formation of these by-products reduces conversion of acetic acid to ethanol.

Ethanol may also be produced via the hydrogenation of acetaldehyde. In theoretical embodiments, ethanol is the only product of acetaldehyde hydrogenation (aside from small amounts of side reaction-generated impurities and/or by-products). In these cases, water is not co-produced with ethanol, as is the case in the hydrogenation of acetic acid. Thus, the resources required for removing impurities in an acetaldehyde hydrogenation process may be significantly less than in an acetic acid hydrogenation process. Accordingly, in some embodiments, the processes of the present invention advantageously use the hydrogenation of acetaldehyde to yield ethanol mixtures that contain few impurities and by-products.

In addition, without being bound by theory, the hydrogenation of acetic acid is believed to proceed through two reaction steps. The first step is endothermic and produces acetaldehyde. The second step is the hydrogenation of the acetaldehyde to form the ethanol. This step is faster and is exothermic. Unlike the hydrogenation of acetic acid, the hydrogenation of acetaldehyde is not believed to involve an endothermic step. As a result, the hydrogenation of acetaldehyde, advantageously, may be carried out at a lower reactor temperature than the hydrogenation of acetic acid.

In one embodiment, the present invention is to a process for producing an ethanol mixture comprising the step of hydrogenating an acetaldehyde feed stream to produce the ethanol mixture, wherein the ethanol mixture comprises methanol and either or both acetic acid and/or ethanol. It has now been discovered that the addition of acetic acid and/or ethanol to the acetaldehyde in the feed stream surprisingly and unexpectedly improves hydrogenation and increases acetaldehyde conversion. Thus, in one embodiment, the acetaldehyde feed stream comprises one or more acetaldehydes and at least one of acetic acid and ethanol. Preferably, the acetaldehyde feed stream comprises a mixture of acetaldehyde and acetic acid, a mixture of acetaldehyde and ethanol, or a mixture of acetaldehyde, acetic acid, and ethanol. In preferred embodiments, the acetaldehyde feed stream comprises from 25 wt. % to 90 wt. % acetaldehyde, e.g., from 30 wt. % to 75 wt. % or from 40 wt. % to 60 wt. % acetaldehyde. In addition to the acetaldehyde, acetic acid, and/or ethanol, the acetaldehyde feed stream may comprise additional components, such as, but not limited to, propanoic acid, water, and esters.

As indicated above, in one embodiment, the acetaldehyde feed stream comprises acetaldehyde and acetic acid. The acetic acid may be hydrogenated under the same conditions as the acetaldehyde is hydrogenated. In this embodiment, in addition to acetaldehyde, the feed stream preferably comprises less than 50 wt. % acetic acid, e.g., less than 45 wt. % or less than 40 wt. %. In terms of ranges, the acetaldehyde feed stream may comprise acetic acid in an amount ranging from 10 wt. % to 75 wt. %, e.g., from 25 wt. % to 70 wt. % or from 40 wt. % to 60 wt. %.

In another embodiment, the acetaldehyde feed stream comprises acetaldehyde and ethanol. Preferably, the ethanol passes through the reaction scheme substantially unaltered. The ethanol preferably does not substantially affect the hydrogenation of the acetaldehyde. When ethanol is present in the feed stream in addition to the acetaldehyde, the acetaldehyde feed stream preferably comprises less than 75 wt. % ethanol, e.g., less than 60 wt. % or less than 50 wt. %. In terms of ranges, the acetaldehyde feed stream optionally comprises ethanol in an amount ranging from 10 wt. % to 75 wt. %, e.g., from 25 wt. % to 70 wt. % or from 40 wt. % to 60 wt. %.

In one embodiment, the acetaldehyde in the acetaldehyde feed stream is obtained from a by-product stream of a vinyl acetate production process. Vinyl acetate is typically formed through the acetoxylation of ethylene. In this reaction, ethylene and acetic acid react in the presence of oxygen to form vinyl acetate and, in some cases, by-products such as acetaldehyde. Suitable catalysts for vinyl acetate production may include, for example, any of those described in GB1559540, U.S. Pat. Nos. 5,185,308; 5,691,267; 6,114,571; and 6,603,038, the disclosures of which are incorporated herein by reference. In a preferred embodiment, the catalyst comprises palladium and gold, optionally on a catalyst support. In conventional vinyl acetate synthesis processes, acetaldehyde is commonly separated from the vinyl acetate and oxidized to produce acetic acid, which is recycled to the vinyl acetate production process. In addition, acetaldehyde may be reacted with anhydrides to yield ethylidene diesters, as described in U.S. Pat. Nos. 2,859,241 and 2,425,389, the disclosures of which are incorporated by reference.

In one aspect of the present invention, the acetaldehyde is recovered to form the acetaldehyde feed stream, at least a portion of which is directed to a hydrogenation reactor for conversion to ethanol. In some embodiments of the present invention, for example, all or a portion of the acetaldehyde in the vinyl acetate by-product stream is hydrogenated to form ethanol. The acetaldehyde-containing by-product stream from a vinyl acetate production facility may comprise, for example, at least 95 wt. % acetaldehyde, e.g., at least 97 wt. % or at least 99 wt. % acetaldehyde. In terms of ranges, the by-product stream preferably comprises from 95 to 99.9 wt. % acetaldehyde, e.g., from 97 to 99.5 wt. % acetaldehyde. The by-product streams, may contain small amounts, e.g., less than 1 wt. % or less than 0.1 wt. %, of impurities such as acrolein, methyl acetate, ethyl acetate, methyl formate, crotonaldehyde, propionaldehyde, propionic acid, vinyl acetate, and benzene. In terms of ranges, the by-product stream may comprise from 0.01 to 1 wt. % of each of these components.

Preferably, the vinyl acetate by-product stream is hydrogenated in the presence of a catalyst that is also effective for the hydrogenation of acetic acid to form ethanol. As a result, the vinyl acetate by-product stream may be combined with acetic acid (and/or ethanol) before hydrogenation. In these cases, the by-product stream, along with acetic acid and/or ethanol, may be vaporized before hydrogenation and the resulting vaporized feed stream is introduced into the hydrogenation reactor.

In addition to being formed as a by-product of a vinyl acetate synthesis process, acetaldehyde also may be formed during the hydrogenation of acetic acid as described in U.S. Pub. No. 2010/0029993, the entirety of which is incorporated herein by reference. In one embodiment, the acetaldehyde employed in the acetaldehyde feed stream is formed from the combination of a vinyl acetate by-product stream and acetaldehyde produced from acetic acid hydrogenation. Acetaldehyde also may be formed in the oxidation of ethylene by the Wacker process. Acetaldehyde may also be produced, for example, by the oxo process in which olefins are hydroformylated with carbon monoxide and hydrogen. The acetaldehyde employed in the acetaldehyde feed stream of the invention may alternatively be derived by any of these acetaldehyde synthesis processes.

In addition to the acetaldehyde, and either or both acetic acid and ethanol, the acetaldehyde feed stream may further comprise one or more other components such as carboxylic acids, anhydrides, acetone, ethyl acetate, water, and mixtures thereof. In some embodiments, the presence of carboxylic acids, such as propanoic acid or its anhydride, may be beneficial in producing propanol.

In one embodiment, the catalyst for hydrogenating the acetaldehyde feed stream comprises a first metal, a silicaceous support, and a support modifier. The catalyst preferably catalyzes the hydrogenation of acetaldehyde and, if present, acetic acid. Suitable hydrogenation catalysts may comprise a first metal. Preferably, the catalysts may also comprise one or more of a second metal, a third metal, or additional metals. The first and optional second and third metals may be selected from any Group IB, IIB, IIIB, IVB, VB, VIB, VIIB, VIII transitional metal, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, silver/palladium, copper/palladium, nickel/palladium, gold/palladium, ruthenium/rhenium, and ruthenium/iron. Exemplary catalysts are further described in U.S. Pat. No. 7,608,744 and U.S. Publication Nos. 2010/0029995 and 2010/0197485, the entire contents and disclosures of which are incorporated herein by reference.

In one embodiment, the first metal is selected from the group consisting of copper, iron, cobalt, nickel, ruthenium, rhodium, palladium, osmium, iridium, platinum, titanium, zinc, chromium, rhenium, molybdenum, and tungsten. In another embodiment, the first metal is selected from the group consisting of platinum, palladium, cobalt, nickel, and ruthenium. Preferably, the first metal is platinum or palladium. Due to its high demand, when the first metal comprises platinum, the catalyst preferably comprises platinum in an amount less than 5 wt. %, e.g., less than 3 wt. %, less than 1 wt. %, or less than 0.1 wt. %.

As indicated above, the catalyst optionally further comprises a second metal, which may function as a promoter. If present, the second metal may be selected from the group consisting of copper, molybdenum, tin, chromium, iron, cobalt, vanadium, tungsten, palladium, platinum, lanthanum, cerium, manganese, ruthenium, rhenium, gold, and nickel. Preferably, the second metal is selected from the group consisting of copper, tin, cobalt, rhenium, and nickel. More preferably, the second metal is tin or rhenium.

If the catalyst comprises two or more metals, e.g., a first metal and a second metal, the first metal optionally is present in the catalyst in an amount from 0.1 to 10 wt. %, e.g., from 0.1 to 5 wt. %, or from 0.1 to 3 wt. %. The second metal optionally is present in an amount from 0.1 and 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The metal ratio may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When included in the catalyst, the third metal preferably is present in an amount from 0.05 and 4 wt. %, e.g., from 0.1 to 3 wt. %, or from 0.1 to 2 wt. %.

In addition to one or more metals, the catalyst may further comprise a support or a modified support, meaning a support that includes a support material and a support modifier, which adjusts the acidity of the support material. The total weight of the support or modified support, based on the total weight of the catalyst, preferably is from 75 wt. % to 99.9 wt. %, e.g., from 78 wt. % to 97 wt. %, or from 80 wt. % to 95 wt. %. In preferred embodiments that use a modified support, the support modifier is present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

In some embodiments, as indicated above, the catalyst support is modified with a support modifier. In preferred embodiments, the support modifier is a basic modifier that has a low volatility or no volatility. Preferably, the modifier remains on the catalyst during the reaction period, e.g., the modifier is not removed from the support as a result of volatility or chromatographic effects. Thus, the modifier does not require in situ replacement. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. Preferably, the support modifier is a calcium silicate, and more preferably calcium metasilicate ($CaSiO_3$). If the support modifier comprises calcium metasilicate, it is preferred that at least a portion of the calcium metasilicate is in crystalline form.

A preferred silica support material is SS61138 High Surface Area (HSA) Silica Catalyst Carrier from Saint-Gobain NorPro. The Saint-Gobain NorPro SS61138 silica contains approximately 95 wt. % high surface area silica; a surface area of about 250 m$^2$/g; a median pore diameter of about 12 nm; an average pore volume of about 1.0 cm$^3$/g as measured by mercury intrusion porosimetry and a packing density of about 0.352 g/cm$^3$ (22 lb/ft$^3$).

A preferred silica/alumina support material is KA-160 (Sud Chemie) silica spheres having a nominal diameter of about 5 mm, a density of about 0.562 g/ml, in absorptivity of about 0.583 g H$_2$O/g support, a surface area of about 160 to 175 m$^2$/g, and a pore volume of about 0.68 ml/g.

As will be appreciated by those of ordinary skill in the art, support materials are selected such that the catalyst system is suitably active, selective, and robust under the process conditions employed for the formation of ethanol.

The metals of the catalysts may be dispersed throughout the support, coated on the outer surface of the support (egg shell) or decorated on the surface of the support.

The catalyst compositions suitable for use with the present invention preferably are formed through metal impregnation of the modified support, although other processes such as chemical vapor deposition may also be employed. Such impregnation techniques are described in U.S. Pat. No. 7,608,744, U.S. Publication Nos. 2010/0029995, and 2010/0197485, referred to above, the entireties of which are incorporated herein by reference.

Some embodiments of the inventive process may employ configurations using a fixed bed reactor and/or a fluidized bed reactor, as one of skill in the art will readily appreciate. In many embodiments of the present invention, an "adiabatic" reactor can be used; that is, there is little or no need for internal plumbing through the reaction zone to add or remove heat. In other embodiments, radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. In one embodiment when the acetaldehyde feed stream comprises acetaldehyde and ethanol, the reaction temperature may range from 125° C. to 300° C., e.g., from 150° C. to 275° C. or 175° C. to 250° C. The pressure may range from 10 KPa to 3000 KPa (about 1.5 to 435 psi), e.g., from 50 KPa to 2300 KPa, or from 100 KPa to 1500 KPa. The reactants may be fed to the reactor at a gas hourly space velocity (GHSV) of greater than 500 hr$^{-1}$, e.g., greater than 1000 hr$^{-1}$, greater than 2500 hr$^{-1}$ or even greater than 5000 hr$^{-1}$. In terms of ranges the GHSV may range from 50 hr$^{-1}$ to 50,000 hr$^{-1}$, e.g., from 500 hr$^{-1}$ to 30,000 hr$^{-1}$, from 1000 hr$^{-1}$ to 10,000 hr$^{-1}$, or from 1000 hr$^{-1}$ to 6500 hr$^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 hr$^{-1}$ or 6,500 hr$^{-1}$.

Although the reaction consumes two moles of hydrogen per mole of acetaldehyde or acetic acid, if present, to produce one mole of ethanol, the molar ratio of hydrogen to acetaldehyde in the feed stream may range from about 20:1 to 1:20, e.g., from 10:1 to 1:10, or from 8:1 to 1:8. In one embodiment, the molar ratio of hydrogen to acetic acid may range from about 20:1 to 1:20, e.g., from 10:1 to 1:10, or from 8:1 to 1:8. In one embodiment, the molar ratio of hydrogen to acetaldehyde is greater than 2:1, e.g., greater than 4:1 or greater than 8:1. In another embodiment, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The raw materials of hydrogen and optionally acetic acid and/or ethanol, used in connection with the process of this invention may be derived from any suitable source including natural gas, petroleum, coal, biomass, and so forth. As examples, acetic acid, if present in the feed, may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624, 7,115,772, 7,005,541, 6,657,078, 6,627,770, 6,143,930, 5,599,976, 5,144,068, 5,026,908, 5,001,259, and 4,994,608, the disclosures of which are incorporated by reference. In one embodiment, when ethanol is present in the feed, the ethanol may be obtained from the ethanol mixture produced by the hydrogenation of the acetaldehyde feed stream.

The acetaldehyde, and, if present, acetic acid, and/or ethanol, may be vaporized in a vaporizer, optionally to the reaction temperature, prior to being introduced into the hydrogenation reactor. The vaporized acetaldehyde feed stream then may be fed along with hydrogen in an undiluted state or the vaporized acetaldehyde feed stream may be diluted with a relatively inert carrier gas, such as nitrogen, argon, helium, carbon dioxide and the like. For reactions run in the vapor phase, the temperature should be controlled in the system such that it does not fall below the dew point of acetaldehyde. In one embodiment, the acetaldehyde is vaporized at the boiling point of acetaldehyde at the particular pressure, and then the vaporized acetaldehyde is further heated to the reactor inlet temperature. In another embodiment the acetaldehyde is transferred to the vapor state by passing hydrogen, recycle gas, another suitable gas, or mixtures thereof through the acetaldehyde at a temperature below the boiling point of acetaldehyde, thereby humidifying the carrier gas with acetaldehyde vapors, followed by heating the mixed vapors up to the reactor inlet temperature. In one embodiment, the acetaldehyde feed includes acetic acid in addition to acetaldehyde, and the acetic acid is vaporized at the boiling point of acetic acid at the particular pressure, and then the vaporized acetic acid may be further heated to the reactor inlet temperature. In another embodiment, the acetic acid is transferred to the vapor state by passing hydrogen, recycle gas, another suitable gas, or mixtures thereof through the acetic acid at a temperature below the boiling point of acetic acid, thereby humidifying the carrier gas with acetic acid vapors, followed by heating the mixed vapors up to the reactor inlet temperature. Preferably, the acetaldehyde, and, if present, acetic acid and/or ethanol is transferred to the vapor by passing hydrogen and/or recycle gas through the acetaldehyde, and acetic acid and/or ethanol at a temperature at or below 125° C., followed by heating of the combined gaseous stream to the reactor inlet temperature.

In some embodiments, the hydrogenation of acetaldehyde, as well as the hydrogenation of acetic acid (if present), may achieve favorable conversion of acetaldehyde and, optionally, acetic acid and favorable selectivity and productivity to ethanol. For purposes of the present invention, the term "conversion" refers to the amount of a specified component, e.g., acetaldehyde or, optionally, acetic acid, in the feed that is converted to another compound. Conversion is expressed as a mole percentage based on the amount of acetaldehyde or acetic acid (whichever is specified) in the feed. For acetaldehyde, the conversion preferably is at least 75%, e.g., at least 85%, or at least 90%. If acetic acid is present in the feed, the acetic acid conversion may be at least 10%, e.g., at least 20%, at least 40%, at least 50%, at least 60%, at least 70%, or at least 80%. Although catalysts that catalyze at high conversions, e.g., at least 80% or at least 90%, for acetaldehyde and/or acetic acid (if present) are desirable, in some embodiments a low conversion may be acceptable where there is a high ethanol selectivity. It is within the scope of the invention to compensate for lower conversion by using appropriate recycle streams or larger reactors. It may be, however, more difficult to compensate for poor selectivity.

Selectivity is expressed as a mole percent based on the specified converted reactant, e.g., acetaldehyde and/or acetic acid. For example, if 30 mole % of the converted acetaldehyde is converted to ethanol, the ethanol selectivity is referred to as 30%. Preferably, the selectivity of acetaldehyde and/or acetic acid to ethanol is at least 80%, e.g., at least 85%, at least 88%, at least 90%, or at least 95%. In one embodiment, the selectivity of acetaldehyde to ethanol is higher than the selectivity of acetic acid to ethanol, e.g., at least 10% higher, at least 25% higher, or at least 50% higher. In preferred embodiments, the hydrogenation process also has a low selectivity to undesirable products, such as methane, ethane, and carbon dioxide. The selectivity to these undesirable products preferably is less than 4%, e.g., less than 2% or less than 1%. More preferably, these undesirable products are not readily detectable in the product. In one embodiment, formation of alkanes is low. For example, in one aspect less than 2%, less than 1%, or less than 0.5% of the acetaldehyde and/or acetic acid passed over the catalyst may be converted to alkanes, which have little value other than as fuel.

The term "productivity," as used herein, refers to the grams of a specified product, e.g., ethanol, formed during the hydrogenation based on the kilograms of catalyst used per hour. A productivity of at least 200 grams of ethanol per kilogram catalyst per hour, e.g., at least 400 or at least 600, is preferred. In terms of ranges, the productivity preferably is from 200 to 3,000 grams of ethanol per kilogram catalyst per hour, e.g., from 400 to 2,500 or from 600 to 2,000.

In various embodiments, the crude reaction effluent, e.g., ethanol mixture, before any subsequent processing, such as purification and separation, will typically comprise ethanol, water, and minor amounts of (unreacted)acetaldehyde, ethyl acetate, acetals, and acetone, and optionally (unreacted) acetic acid. Exemplary embodiments of crude ethanol compositional ranges are provided in Table 1. It should be understood that ethanol mixture may contain other components, not listed, such as other components in the feed.

TABLE 1

ETHANOL MIXTURES

| Component | Conc. (wt. %) | Conc. (wt. %) | Conc. (wt. %) |
| --- | --- | --- | --- |
| Ethanol | 50 to 97 | 55 to 95 | 60 to 95 |
| Water | 0.1 to 25 | 1 to 25 | 2 to 20 |
| Acetaldehyde | <10 | <3 | <2 |
| Acetic Acid | 10 to 95 | 10 to 30 | 15 to 25 |
| Ethyl Acetate | <10 | <8 | <5 |
| Acetone | <5 | <1 | <0.1 |
| Acetals | <5 | <2 | <1 |

The amounts indicated as less than (<) in the tables throughout present application are preferably not present, but if present, may be present in trace amounts or in amounts greater than 0.0001 wt. %.

In one embodiment, the ethanol mixtures may be purified in one or more distillation columns to remove impurities. Suitable purification systems are described in co-pending U.S. application Ser. Nos. 12/852,227, 12/852,269, and 12/833,737, the disclosures of which are incorporated by reference. Advantageously, the present invention provides a crude ethanol mixture that contains lower amounts of other products, e.g., ethyl acetate. Thus, the resources required to separate these other products from ethanol is reduced.

Figure 2:
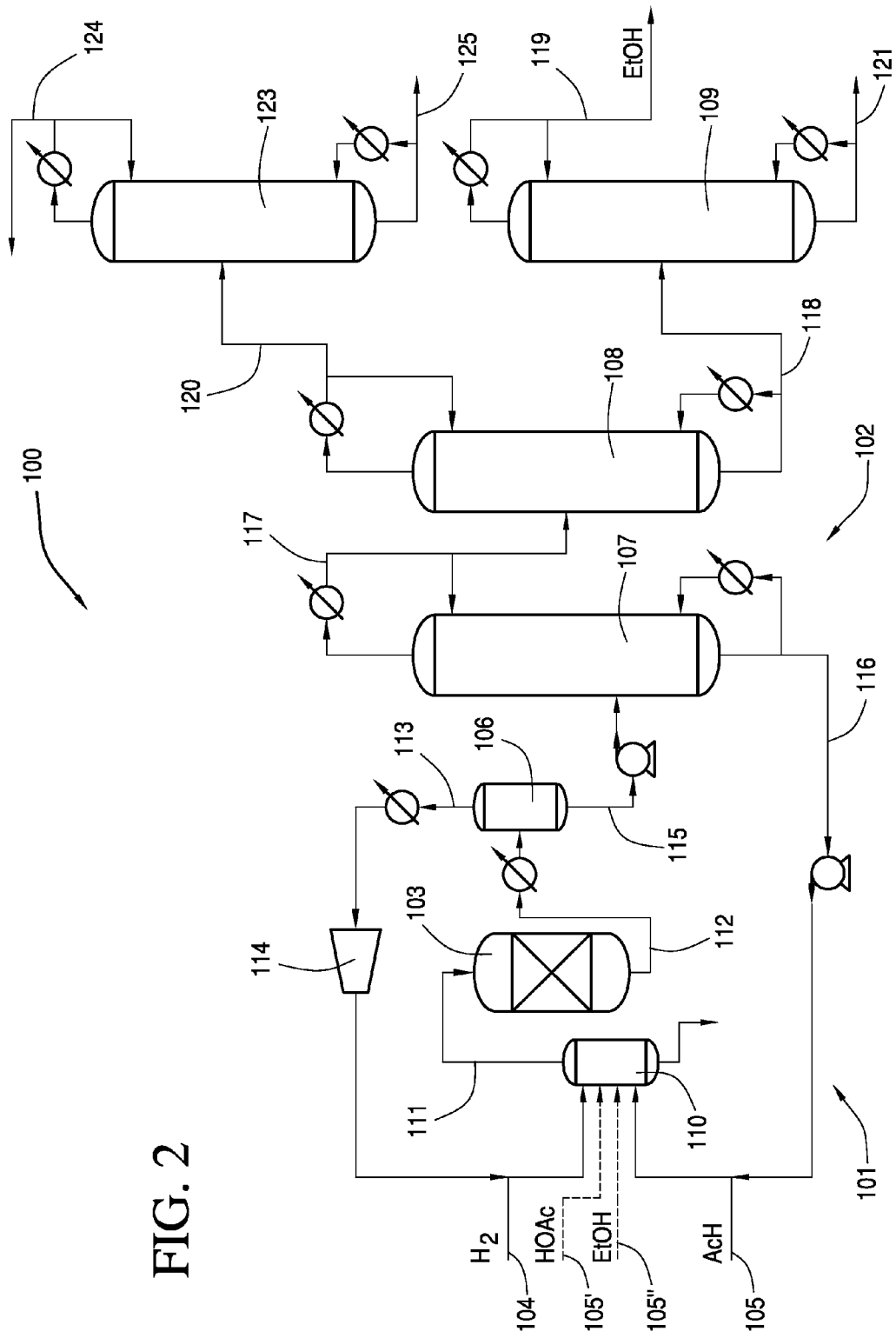
FIG. 2 is a schematic diagram of a hydrogenation system having four separation columns in accordance with one embodiment of the present invention.

FIGS. 1 and 2 show a hydrogenation system 100 suitable for the hydrogenation of acetaldehyde, and optionally acetic acid, and the separation of ethanol from the crude reaction mixture according to one embodiment of the invention. System 100 comprises reaction zone 101 and distillation zone 102. Reaction zone 101 comprises reactor 103, hydrogen feed line 104, acetaldehyde feed line 105, optional acetic acid feed line 105', and optional ethanol feed line 105". In preferred embodiments, acetaldehyde feed line 105 is obtained from a by-product stream of a vinyl acetate production process.

In FIG. 1, distillation zone 102 comprises flasher 106, first column 107, second column 108, and third column 109. In FIG. 2, distillation zone 102 further comprises a fourth column 123. Hydrogen and acetaldehyde, and optionally acetic acid and/or ethanol, are fed to vaporizer 110 via lines 104, 105, 105' and 105", respectively, to create a vapor feed stream in line 111. Line 111 is directed to reactor 103. In one embodiment, lines 104 and 105 may be combined and jointly fed to the vaporizer 110, e.g., in one stream containing both hydrogen and acetaldehyde. The temperature of the vapor feed stream in line 111 is preferably from 100° C. to 350° C., e.g., from 120° C. to 310° C. or from 150° C. to 300° C. Any feed that is not vaporized is removed from vaporizer 110, as shown in FIGS. 1 and 2, and may be recycled thereto. In addition, although FIGS. 1 and 2 shows line 111 being directed to the top of reactor 103, line 111 may be directed to the side, upper portion, or bottom of reactor 103. Further modifications and additional components to reaction zone 101 are described below.

Reactor 103 contains the catalyst that is used in the hydrogenation of acetaldehyde. Preferably, the catalyst is also used in the hydrogenation of the carboxylic acid, e.g., acetic acid. In one embodiment, one or more guard beds (not shown) may be used to protect the catalyst from poisons or undesirable impurities contained in the feed or return/recycle streams. Such guard beds may be employed in the vapor or liquid streams. Suitable guard bed materials are known in the art and include, for example, carbon, silica, alumina, ceramic, or resins. In one aspect, the guard bed media is functionalized to trap particular species such as sulfur or halogens. During the hydrogenation process, a crude ethanol product is withdrawn, preferably continuously, from reactor 103 via line 112. The crude ethanol product may be condensed and fed to flasher 106, which, in turn, provides a vapor stream and a liquid stream. The flasher 106 preferably operates at a temperature of from 50° C. to 500° C., e.g., from 70° C. to 400° C. or from 100° C. to 350° C. The pressure of flasher 106 preferably is from 50 KPa to 2000 KPa, e.g., from 75 KPa to 1500 KPa or from 100 to 1000 KPa. In one preferred embodiment the temperature and pressure of the flasher is similar to the temperature and pressure of the reactor 103.

The vapor stream exiting the flasher 106 may comprise hydrogen and hydrocarbons, which may be purged and/or returned to reaction zone 101 via line 113. As shown in FIGS. 1 and 2, the returned portion of the vapor stream passes through compressor 114 and is combined with the hydrogen feed and co-fed to vaporizer 110.

The liquid from flasher 106 is withdrawn and pumped as a feed composition via line 115 to the side of first column 107, also referred to as the acid separation column. The contents of line 115 typically will be substantially similar to the product obtained directly from the reactor, and may, in fact, also be characterized as a crude ethanol product. However, the feed composition in line 115 preferably has substantially no hydrogen, carbon dioxide, methane, or ethane, which are removed by flasher 106. Exemplary components of liquid in line 115 are provided in Table 2. It should be understood that liquid line 115 may contain other components, not listed, such as components in the feed.

TABLE 2

FEED COMPOSITION

| | Conc. (wt. %) | Conc. (wt. %) | Conc. (wt. %) |
|---|---|---|---|
| Ethanol | 50 to 97 | 55 to 95 | 60 to 95 |
| Acetic Acid | 10 to 95 | 10 to 30 | 15 to 25 |
| Water | 0.1 to 25 | 1 to 25 | 2 to 20 |
| Ethyl Acetate | <10 | 0.001 to 8 | 1 to 5 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout present application are preferably not present, but if present, may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol or mixtures thereof. In one embodiment, the feed composition, e.g., line 115, may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

In embodiments where the acetaldehyde feed stream comprises acetaldehyde and ethanol, the crude reaction product preferably comprises less than less than 5 wt. % acetic acid. Under these conditions, acid separation column 107 may be skipped and line 115 may be introduced directly to second column 108. Second column 108 may be referred to herein as a "light ends column." Also, in embodiments where the acetaldehyde feed stream comprises acetaldehyde and acetic acid and the conversion of acetic acid is high, acid separation column 107 may be skipped. In these cases, the liquid in line 116 may comprise less than 5 wt. % liquid, e.g., less than 3%.

In the embodiment shown in FIG. 1, line 115 is introduced in the lower part of first column 107, e.g., lower half or lower third. In a preferred embodiment, first column 107 may be used to remove unreacted acetic acid fed to the reactor 103. In these cases, the feed comprises acetaldehyde and acetic acid. In first column 107, unreacted acetic acid, a portion of the water, and other heavy components, if present, are removed from the composition in line 115 and are withdrawn, preferably continuously, as residue. Some or all of the residue may be returned and/or recycled back to reaction zone 101 via line 116. Although residue is shown as being co-fed with acetaldehyde in FIGS. 1 and 2, residue may be directly fed to vaporizer 110 via line 116. First column 107 also forms an overhead distillate, which is withdrawn in line 117, and which may be condensed and refluxed, for example, at a ratio of from 10:1 to 1:10, e.g., from 3:1 to 1:3 or from 1:2 to 2:1.

Any of columns 107, 108, 109, or 123 may comprise any distillation column capable of separation and/or purification. The columns preferably comprise tray columns having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in FIG. 1. As shown in FIG. 1, heat may be supplied to the base of each column or to a circulating bottom stream through a heat exchanger or reboiler. Other types of reboilers, such as internal reboilers, may also be used in some embodiments. The heat that is provided to reboilers may be derived from any heat generated during the process that is integrated with the reboilers or from an external source such as another heat generating chemical process or a boiler. Although one reactor and one flasher are shown in FIG. 1, additional reactors, flashers, condensers, heating elements, and other components may be used in embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in any of the columns may vary. As a practical matter, pressures from 10 KPa to 3000 KPa will generally be employed in these zones although in some embodiments subatmospheric pressures may be employed as well as superatmospheric pressures. Temperatures within the various zones will normally range between the boiling points of the composition removed as the distillate and the composition removed as the residue. It will be recognized by those skilled in the art that the temperature at a given location in an operating distillation column is dependent on the composition of the material at that location and the pressure of column. In addition, feed rates may vary depending on the size of the production process and, if described, may be generically referred to in terms of feed weight ratios.

When column 107 is operated under standard atmospheric pressure, the temperature of the residue exiting in line 116 from column 107 preferably is from 95° C. to 120° C., e.g., from 105° C. to 117° C. or from 110° C. to 115° C. The temperature of the distillate exiting in line 117 from column 107 preferably is from 70° C. to 110° C., e.g., from 75° C. to 95° C. or from 80° C. to 90° C. In other embodiments, the pressure of first column 107 may range from 0.1 KPa to 510 KPa, e.g., from 1 KPa to 475 KPa or from 1 KPa to 375 KPa. Exemplary components of the distillate and residue compositions for first column 107 are provided in Table 3 below. It should also be understood that the distillate and residue may also contain other components, not listed, such as components in the feed. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

FIRST COLUMN

| | Conc. (wt. %) | Conc. (wt. %) | Conc. (wt. %) |
|---|---|---|---|
| Distillate | | | |
| Ethanol | 20 to 75 | 30 to 70 | 40 to 65 |
| Water | 10 to 40 | 15 to 35 | 20 to 35 |
| Acetic Acid | <2 | 0.001 to 0.5 | 0.01 to 0.2 |
| Ethyl Acetate | <60 | 5.0 to 40 | 10 to 30 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue | | | |
| Acetic Acid | 60 to 100 | 70 to 95 | 85 to 92 |
| Water | <30 | 1 to 20 | 1 to 15 |
| Ethanol | <1 | <0.9 | <0.07 |

As shown in Table 3, without being bound by theory, it has surprisingly and unexpectedly been discovered that when any amount of acetal is detected in the feed that is introduced to the acid separation column (first column 107), the acetal appears to decompose in the column such that less or even no detectable amounts are present in the distillate and/or residue.

Depending on the reaction conditions, the crude ethanol product exiting reactor 103 in line 112 may comprise ethanol, acetaldehyde (unconverted), ethyl acetate, water and optionally acetic acid (unconverted). After exiting reactor 103, a non-catalyzed equilibrium reaction may occur between the components contained in the crude ethanol product until it is added to flasher 106 and/or first column 107. This equilibrium reaction tends to drive the crude ethanol product to an equilibrium between ethanol/acetic acid and ethyl acetate/water.

The distillate, e.g., overhead stream, of column 107 optionally is condensed and refluxed as shown in FIG. 1, preferably, at a reflux ratio of 1:5 to 10:1. The distillate in line 117 preferably comprises ethanol, ethyl acetate, and water, along with other impurities, which may be difficult to separate due to the formation of binary and tertiary azeotropes.

The first distillate in line 117 is introduced to the second column 108, preferably in the middle part of column 108, e.g., middle half or middle third. As one example, when a 25 tray column is used in a column without water extraction, line 117 is introduced at tray 17. In one embodiment, the second column 108 may be an extractive distillation column. In such embodiments, an extraction agent, such as water, may be added to second column 108. If the extraction agent comprises water, it may be obtained from an external source or from an internal return/recycle line from one or more of the other columns.

Second column 108 may be a tray column or packed column. In one embodiment, second column 108 is a tray column having from 5 to 70 trays, e.g., from 15 to 50 trays or from 20 to 45 trays.

Although the temperature and pressure of second column 108 may vary, when at atmospheric pressure the temperature of the second residue exiting in line 118 from second column 108 preferably is from 60° C. to 90° C., e.g., from 70° C. to 90° C. or from 80° C. to 90° C. The temperature of the second distillate exiting in line 120 from second column 108 preferably is from 50° C. to 90° C., e.g., from 60° C. to 80° C. or from 60° C. to 70° C. Column 108 may operate at atmospheric pressure. In other embodiments, the pressure of second column 108 may range from 0.1 KPa to 510 KPa, e.g., from 1 KPa to 475 KPa or from 1 KPa to 375 KPa. Exemplary components for the distillate and residue compositions for second column 108 are provided in Table 4 below. It should be understood that the distillate and residue may also contain other components, not listed, such as components in the feed.

TABLE 4

SECOND COLUMN

| | Conc. (wt. %) | Conc. (wt. %) | Conc. (wt. %) |
|---|---|---|---|
| Distillate | | | |
| Ethyl Acetate | 10 to 90 | 25 to 90 | 50 to 90 |
| Acetaldehyde | 1 to 25 | 1 to 15 | 1 to 8 |
| Water | 1 to 25 | 1 to 20 | 4 to 16 |
| Ethanol | <30 | 0.001 to 15 | 0.01 to 5 |
| Acetal | <5 | 0.001 to 2 | 0.01 to 1 |
| Residue | | | |
| Water | 30 to 70 | 30 to 60 | 30 to 50 |
| Ethanol | 20 to 75 | 30 to 70 | 40 to 70 |
| Ethyl Acetate | <3 | 0.001 to 2 | 0.001 to 0.5 |
| Acetic Acid | <0.5 | 0.001 to 0.3 | 0.001 to 0.2 |

The weight ratio of ethanol in the second residue to ethanol in the second distillate preferably is at least 3:1, e.g., at least 6:1, at least 8:1, at least 10:1 or at least 15:1. The weight ratio of ethyl acetate in the second residue to ethyl acetate in the second distillate preferably is less than 0.4:1, e.g., less than 0.2:1 or less than 0.1:1. In embodiments that use an extractive column with water as an extraction agent as the second column 108, the weight ratio of ethyl acetate in the second residue to ethyl acetate in the second distillate approaches zero.

As shown, the second residue from the bottom of second column 108, which comprises ethanol and water, is fed via line 118 to third column 109, also referred to as the "product column." More preferably, the second residue in line 118 is introduced in the lower part of third column 109, e.g., lower half or lower third. Third column 109 recovers ethanol, which preferably is substantially pure other than the azeotropic water content, as the distillate in line 119. The distillate of third column 109 preferably is refluxed as shown in FIG. 1, for example, at a reflux ratio of from 1:10 to 10:1, e.g., from 1:3 to 3:1 or from 1:2 to 2:1. The third residue in line 121, which preferably comprises primarily water, preferably is removed from the system 100 or may be partially returned to any portion of the system 100. Third column 109 is preferably a tray column as described above and preferably operates at atmospheric pressure. The temperature of the third distillate exiting in line 119 from third column 109 preferably is from 60° C. to 110° C., e.g., from 70° C. to 100° C. or from 75° C. to 95° C. The temperature of the third residue exiting from third column 109 preferably is from 70° C. to 115° C., e.g., from 80° C. to 110° C. or from 85° C. to 105° C., when the column is operated at atmospheric pressure. Exemplary components of the distillate and residue compositions for third column 109 are provided in Table 5 below. It should be understood that the distillate and residue may also contain other components, not listed, such as components in the feed.

TABLE 5

THIRD COLUMN

|  | Conc. (wt. %) | Conc. (wt. %) | Conc. (wt. %) |
|---|---|---|---|
| Distillate |  |  |  |
| Ethanol | 75 to 96 | 80 to 96 | 85 to 96 |
| Water | <12 | 1 to 9 | 3 to 8 |
| Acetic Acid | <1 | 0.001 to 0.1 | 0.005 to 0.01 |
| Ethyl Acetate | <5 | 0.001 to 4 | 0.01 to 3 |
| Residue |  |  |  |
| Water | 75 to 100 | 80 to 100 | 90 to 100 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |

Any of the compounds that are carried through the distillation process from the feed or crude reaction product generally remain in the third distillate in amounts of less 0.1 wt. %, based on the total weight of the third distillate composition, e.g., less than 0.05 wt. % or less than 0.02 wt. %. In one embodiment, one or more side streams may remove impurities from any of the columns 107, 108, 109 and/or 123 in the system 100. Preferably at least one side stream is used to remove impurities from the third column 109. The impurities may be purged and/or retained within the system 100.

The third distillate in line 119 may be further purified to form an anhydrous ethanol product stream, i.e., "finished anhydrous ethanol," using one or more additional separation systems, such as, for example, distillation columns (e.g., a finishing column) or molecular sieves.

Returning to second column 107, the second distillate preferably is refluxed as shown in FIG. 1, for example, at a reflux ratio of from 1:10 to 10:1, e.g., from 1:5 to 5:1 or from 1:3 to 3:1. In FIG. 1, the second distillate may be purged or recycled back to the reaction zone 101. In FIG. 2, the second distillate is fed via line 120 to fourth column 123, also referred to as the "acetaldehyde removal column." Preferably, fourth column 123 may be used when the amount of acetaldehyde, either unreacted acetaldehyde or a by-product of optional acetic acid hydrogenation, is greater than 1 wt. %, e.g., greater than 3 wt. % or greater than 5 wt. %.

In fourth column 123, the second distillate is separated into a fourth distillate in line 124, which comprises acetaldehyde, and a fourth residue in line 125, which comprises ethyl acetate. The fourth distillate preferably is refluxed at a reflux ratio of from 1:20 to 20:1, e.g., from 1:15 to 15:1 or from 1:10 to 10:1, and a portion of the fourth distillate is returned to the reaction zone 101. In one embodiment, a portion of the fourth distillate is purged. For example, the fourth distillate may be combined with the acetic acid feed, if present, added to the vaporizer 110, or added directly to the reactor 103. In one embodiment, the fourth distillate is co-fed with the acetaldehyde in feed line 105 to vaporizer 110. Optionally, fourth distillate may be co-fed with acetic acid feed line 105', if present, or ethanol feed line 105".

Without being bound by theory, since the processes of the present invention hydrogenate acetaldehyde to form ethanol, the recycling to the reaction zone of a stream that contains acetaldehyde, e.g., stream 124, increases the yield of ethanol and decreases by-product and waste generation. In another embodiment (not shown), the acetaldehyde may be collected and used, with or without further purification, to make useful products including but not limited to n-butanol, 1,3-butanediol, and/or crotonaldehyde and derivatives.

The fourth residue of fourth column 123 may be purged via line 125. The fourth residue primarily comprises ethyl acetate and ethanol, which may be suitable for use as a solvent mixture or in the production of esters. In one preferred embodiment, the acetaldehyde is removed from the second distillate in fourth column 123 such that no detectable amount of acetaldehyde is present in the residue of column 123.

Fourth column 123 is preferably a tray column as described above and preferably operates above atmospheric pressure. The pressure of fourth column 123 preferably is from 120 KPa to 5,000 KPa, e.g., from 200 KPa to 4,500 KPa, or from 400 KPa to 3,000 KPa. In a preferred embodiment the fourth column 123 may operate at a pressure that is higher than the pressure of the other columns.

The temperature of the fourth distillate exiting in line 124 from fourth column 123 preferably is from 60° C. to 110° C., e.g., from 70° C. to 100° C. or from 75° C. to 95° C. The temperature of the residue exiting from fourth column 125 preferably is from 70° C. to 115° C., e.g., from 80° C. to 110° C. or from 85° C. to 110° C. Exemplary components of the distillate and residue compositions for fourth column 123 are provided in Table 6 below. It should be understood that the distillate and residue may also contain other components, not listed, such as components in the feed.

TABLE 6

FOURTH COLUMN

|  | Conc. (wt. %) | Conc. (wt. %) | Conc. (wt. %) |
|---|---|---|---|
| Distillate |  |  |  |
| Acetaldehyde | 2 to 80 | 2 to 50 | 5 to 40 |
| Ethyl Acetate | <90 | 30 to 80 | 40 to 75 |
| Ethanol | <30 | 0.001 to 25 | 0.01 to 20 |
| Water | <25 | 0.001 to 20 | 0.01 to 15 |
| Residue |  |  |  |
| Ethyl Acetate | 40 to 100 | 50 to 100 | 60 to 100 |
| Ethanol | <40 | 0.001 to 30 | 0 to 15 |
| Water | <25 | 0.001 to 20 | 2 to 15 |
| Acetaldehyde | <1 | 0.001 to 0.5 | Not detectable |
| Acetal | <3 | 0.001 to 2 | 0.01 to 1 |

The ethanol mixtures produced by the embodiments of the present invention may be used in a variety of applications including fuels, solvents, chemical feedstocks, pharmaceutical products, cleansers, sanitizers, hydrogenation transport or consumption. In fuel applications, the ethanol mixtures may be blended with gasoline for motor vehicles such as automobiles, boats and small piston engine aircrafts. In non-fuel applications, the ethanol mixtures may be used as a solvent for toiletry and cosmetic preparations, detergents, disinfectants, coatings, inks, and pharmaceuticals. The ethanol mixtures may also be used as a processing solvent in manufacturing processes for medicinal products, food preparations, dyes, photochemicals and latex processing.

The ethanol mixtures may also be used a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the ethanol mixtures may be esterified with acetic acid or reacted with polyvinyl acetate. The ethanol mixtures may be dehydrated to produce ethylene. Any of known dehydration catalysts can be employed in to dehydrate ethanol, such as those described in copending U.S. Pub. Nos. 2010/0030002 and 2010/0030001, the disclosures of which are incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the disclosures of which are incorporated by reference.

The invention is described in detail below with reference to numerous embodiments for purposes of exemplification and illustration only. Modifications to particular embodiments within the spirit and scope of the present invention, set forth in the appended claims, will be readily apparent to those of skill in the art.

The following examples describe the procedures used for the preparation of various catalysts employed in the process of this invention.

EXAMPLES

Example 1

An acetaldehyde feed stream comprising 50 wt. % acetaldehyde and 50 wt. % acetic acid was hydrogenated in the presence of a catalyst comprising 1.6 wt. % platinum and 1 wt. % tin supported on ⅛ inch calcium silicate modified silica extrudates. The hydrogenation reaction was performed in the vapor phase at a temperature of 250° C., a pressure of 250 psig, and at a GHSV of 4,500 hr$^{-1}$. The composition of the crude ethanol mixture in the reactor effluent is provided in Table 7 below.

Example 2

The acetaldehyde feed stream was hydrogenated as in Example 1, but at a temperature of 300° C. The composition of the crude resultant ethanol mixture in the reactor effluent is provided in Table 7.

Example 3

An acetaldehyde feed stream having 50 wt. % acetaldehyde and 50 wt. % ethanol was hydrogenated under the conditions described in Example 1. The composition of the crude resultant ethanol mixture in the reactor effluent is provided in Table 7.

Example 4

The acetaldehyde feed stream was hydrogenation as in Example 3, but at a temperature of 300° C. The composition of the crude resultant ethanol mixture in the reactor effluent is provided in Table 7.

TABLE 7

| | Example | | | |
|---|---|---|---|---|
| | 1 | 2 | 3 | 4 |
| Feed Stream | | | | |
| Acetaldehyde | 50 wt. % | 50 wt. % | 50 wt. % | 50 wt. % |
| Acetic Acid | 50 wt. % | 50 wt. % | — | — |
| Ethanol | — | — | 50 wt. % | 50 wt. % |
| Hydrogenation Temp. | 250° C. | 300° C. | 250° C. | 300° C. |
| Reactor Effluent | | | | |
| Ethanol | 64.7 wt. % | 71.1 wt. % | 96.1% | 90.4% |
| Water | 7.5 wt. % | 12.5 wt. % | 0.5% | 1.3% |
| Acetic Acid | 24.2 wt. % | 11.5 wt. % | 0.6% | 0.9% |
| Acetaldehyde | 0.2 wt. % | 1.4 wt. % | 0.6% | 1.4% |
| Acetone | 0.01 wt. % | 0.0 wt. % | 0.01% | 0.1% |
| Acetal | 1.7 wt. % | 1.8 wt. % | 0.3% | 0.6% |
| Ethyl Acetate | 4.9 wt. % | 6.4 wt. % | 1.1% | 2.8% |
| Acetaldehyde Conversion | 99.6% | 97.2% | 98.9% | 97% |
| Acetic Acid Conversion | 51.5% | 76.8% | — | — |

For the acetaldehyde/acetic acid feed stream of Examples 1 and 2, the yield of ethanol was greater at the higher temperature. For the acetaldehyde/ethanol feed stream of Examples 3 and 4, the yield of ethanol was greater at the lower temperature. The conversion of acetaldehyde to ethanol is an exothermic reaction and lower reaction temperatures are more beneficial. The conversion of acetic acid to ethanol is believed to involve at least two steps. The first step is the conversion of acetic acid to acetaldehyde, which is endothermic. The second step is the conversion of acetaldehyde to ethanol. The first step is slower than the second step. Also, the first step also yields water as a co-product.

In each of the examples, the conversion of acetaldehyde to ethanol was greater than 96%.

For Examples 3 and 4, the feed stream started with 50 wt. % of ethanol. This ethanol is believed to proceed through the reaction essentially unaltered during the hydrogenation.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing an ethanol mixture, comprising hydrogenating an acetaldehyde feed stream in the presence of a catalyst to form the ethanol mixture, wherein the acetaldehyde feed stream comprises essentially acetaldehyde and acetic acid, wherein the catalyst comprises a first metal, a silicaceous support, and at least one support modifier.

2. The process of claim 1, wherein the acetaldehyde feed stream comprises the acetaldehyde in an amount from 25 wt. % to 90 wt. % and acetic acid in an amount from 10 wt. % to 75 wt. %.

3. The process of claim 1, wherein the acetaldehyde feed stream comprises less than 50 wt. % acetic acid.

4. The process of claim 1, further comprising:
vaporizing the acetaldehyde feed stream to form a vapor feed stream; and
reacting the vapor feed stream in the presence of the catalyst.

5. The process of claim 1, wherein the hydrogenation is performed at a temperature of from 125° C. to 350° C.

6. The process of claim 1, wherein the hydrogenation is performed at a pressure of 10 KPa to 3000 KPa.

7. The process of claim 1, wherein the hydrogenation is performed at a hydrogen to acetaldehyde mole ratio greater than 2:1.

8. The process of claim 1, wherein the conversion of the acetaldehyde in the acetaldehyde feed stream is at least 75% and the conversion of the acetic acid in the acetaldehyde feed stream is at least 10%.

9. The process of claim 1, wherein the ethanol mixture comprises
from 50 wt. % to 97 wt. % ethanol;
from 0.1 wt. % to 25 wt. % water;
less than 35 wt. % acetic acid; and
less than 10 wt. % acetaldehyde.

10. The process of claim 1, further comprising purifying the ethanol mixture in one or more separation units to produce ethanol.

11. The process of claim 1, wherein the first metal is present in an amount of from 0.1 to 25 wt. %, based on the total weight of the catalyst and is selected from the group consisting of copper, iron, cobalt, nickel, ruthenium, rhodium, palladium, osmium, iridium, platinum, titanium, zinc, chromium, rhenium, molybdenum, and tungsten.

12. The process of claim 1, wherein the at least one support modifier is present in an amount of 0.1 wt. % to 50 wt. %, based on the total weight of the catalyst and is selected from the group consisting of (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof.

13. The process of claim 1, wherein the support is present in an amount of 25 wt. % to 99 wt. %, based on the total weight of the catalyst and is selected from the group consisting of silica, silica/alumina, calcium metasilicate, pyrogenic silica, high purity silica and mixtures thereof.

14. The process of claim 1, wherein the catalyst further comprises a second metal different from the first metal, wherein the second metal is present in an amount of from 0.1 to 10 wt. %, based on the total weight of the catalyst and is selected from the group consisting of copper, molybdenum, tin, chromium, iron, cobalt, vanadium, tungsten, palladium, platinum, lanthanum, cerium, manganese, ruthenium, rhenium, gold, and nickel.

15. A process for producing an ethanol mixture, comprising:
contacting a mixture of ethylene and acetic acid with oxygen to produce vinyl acetate and at least one by-product stream comprising from 90 to 99.9 wt. % acetaldehyde; and
hydrogenating at least of a portion the at least one by-product stream in the presence of a catalyst to form the ethanol mixture.

16. The process of claim 15, further comprising:
vaporizing the at least one by-product stream and at least one of acetic acid and ethanol,
to form a vapor feed stream; and
reacting the vapor feed stream in the presence of the catalyst.

17. The process of claim 16, wherein the vapor feed stream comprises from 25 wt. % to 90 wt. % of acetaldehyde and 10 wt. % to 75 wt. % of the at least one of acetic acid and ethanol.

18. The process of claim 16, wherein the catalyst comprises a combination of metals selected from the group consisting of platinum/tin, platinum/ruthenium, platinum/rhenium, palladium/ruthenium, palladium/rhenium, cobalt/palladium, cobalt/platinum, cobalt/chromium, cobalt/ruthenium, silver/palladium, copper/palladium, nickel/palladium, gold/palladium, ruthenium/rhenium, and ruthenium/iron.

* * * * *